US008043294B2

(12) United States Patent
Fencl et al.

(10) Patent No.: US 8,043,294 B2
(45) Date of Patent: Oct. 25, 2011

(54) REFERENCE MARK ADJUSTMENT MECHANISM FOR A FEMORAL CALIPER AND METHOD OF USING THE SAME

(75) Inventors: Robert M. Fencl, Cordova, TN (US); J. David Blaha, Ann Arbor, MI (US); Vernon R. Hartdegen, Collierville, TN (US); William J. Maloney, Clayton, MO (US); Stephen E. White, Cordova, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 354 days.

(21) Appl. No.: 10/794,188

(22) Filed: Mar. 5, 2004

(65) Prior Publication Data

US 2005/0209600 A1    Sep. 22, 2005

(51) Int. Cl.
*A61B 17/58* (2006.01)
(52) U.S. Cl. ......................................................... 606/89
(58) Field of Classification Search ............... 606/86–89, 606/79, 86 R, 96
See application file for complete search history.

(56) References Cited

U.S. PATENT DOCUMENTS

| | | | | |
|---|---|---|---|---|
| 4,298,992 | A | | 11/1981 | Burstein et al. |
| 4,474,177 | A | | 10/1984 | Whiteside |
| 4,566,448 | A | * | 1/1986 | Rohr, Jr. .......................... 606/88 |
| 4,718,413 | A | | 1/1988 | Johnson |
| 4,952,213 | A | * | 8/1990 | Bowman et al. ................. 606/79 |
| 5,219,362 | A | | 6/1993 | Tuke et al. |
| 5,228,459 | A | * | 7/1993 | Caspari et al. ................. 128/898 |
| 5,364,401 | A | | 11/1994 | Ferrante et al. |
| 5,514,143 | A | * | 5/1996 | Bonutti et al. .................. 606/86 |
| 5,562,675 | A | * | 10/1996 | McNulty et al. ................ 606/96 |
| 5,569,261 | A | * | 10/1996 | Marik et al. ..................... 606/88 |
| 5,624,444 | A | * | 4/1997 | Wixon et al. .................... 606/88 |
| 5,662,656 | A | * | 9/1997 | White ............................. 606/88 |
| 5,672,178 | A | | 9/1997 | Petersen |
| 5,681,316 | A | * | 10/1997 | DeOrio et al. .................. 606/88 |
| 5,688,280 | A | * | 11/1997 | Booth et al. .................... 606/88 |

(Continued)

OTHER PUBLICATIONS

Wright Medical Technology, Inc.; Advance® Knee System Single Reference Point, Surgical Technique, Traditional, Medial-Pivot, Posterior Stabilized; © 1998 Wright Medical Technology, Inc., 15 pages.

(Continued)

*Primary Examiner* — Thomas C. Barrett
*Assistant Examiner* — Christopher Beccia
(74) *Attorney, Agent, or Firm* — Womble Carlyle Sandridge & Rice, PLLC

(57) ABSTRACT

A femoral caliper having one or more anatomical referencing members for placement against portions of the femur, such as the anterior cortex and posterior portion of the femoral condyles, to measure the femur for sizing of the femoral component. A reference mark positioning guide of the femoral caliper is connected to the anatomical referencing member and is capable of guiding placement of a reference mark on the femur that facilitates positioning of the femoral component. The femoral caliper includes an adjustment mechanism capable of displacing the reference mark positioning guide relative to the anatomical referencing member. This allows adjustment of the position of the reference mark (and hence the femoral component) on the femur to account for the up or down sizing of the femoral component. Preferably, the adjustment mechanism adjusts the reference mark positioning guide in the anterior-posterior direction to allow balancing of the tightness or laxity of the selected component.

5 Claims, 14 Drawing Sheets

U.S. PATENT DOCUMENTS

| | | | |
|---|---|---|---|
| 5,702,458 | A | 12/1997 | Burstein et al. |
| 5,964,808 | A | 10/1999 | Blaha et al. |
| 6,013,081 | A * | 1/2000 | Burkinshaw et al. ............ 606/88 |
| 6,013,103 | A | 1/2000 | Kaufman et al. |
| 6,022,377 | A * | 2/2000 | Nuelle et al. ..................... 606/90 |
| 6,267,762 | B1 * | 7/2001 | Millard et al. .................... 606/54 |
| 6,290,704 | B1 * | 9/2001 | Burkinshaw et al. ............ 606/88 |
| 6,458,135 | B1 * | 10/2002 | Harwin et al. .................... 606/88 |
| 7,011,664 | B2 * | 3/2006 | Haney et al. ...................... 606/87 |
| 7,029,477 | B2 * | 4/2006 | Grimm .............................. 606/88 |
| 7,261,719 | B1 * | 8/2007 | Twomey et al. ............... 606/102 |
| 7,309,339 | B2 * | 12/2007 | Cusick et al. ..................... 606/88 |
| 7,488,324 | B1 * | 2/2009 | Metzger et al. .................. 606/89 |
| 7,628,793 | B2 * | 12/2009 | Calton et al. ..................... 606/88 |

OTHER PUBLICATIONS

Wright Medical Technology, Inc., Advance® Knee Distal Cut First Surgical Technique, © 2002 Wright Medical Technology, Inc., pp. 1-17.

Wright Medical Technology, Inc.; Advance® Anterior Rough Cut, Surgical Technique, © 2002 Wright Medical Technology, Inc., 20 pages.

Wright Medical Technology, Inc., Advance® Knee Distal Cut First Surgical Technique, © 2002 Wright Medical Technology, Inc., 20 pages.

* cited by examiner

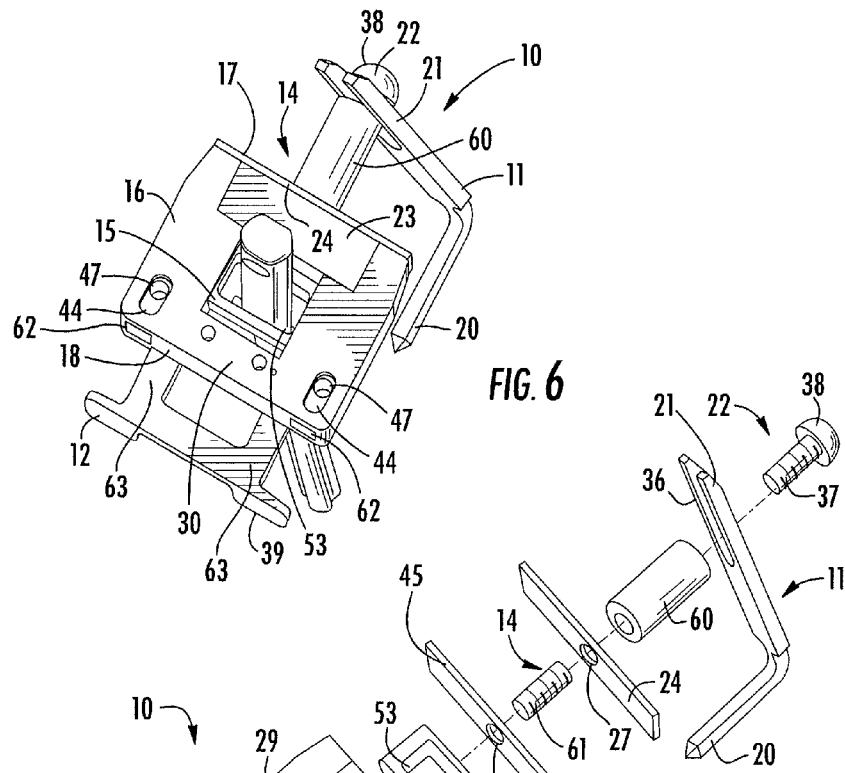
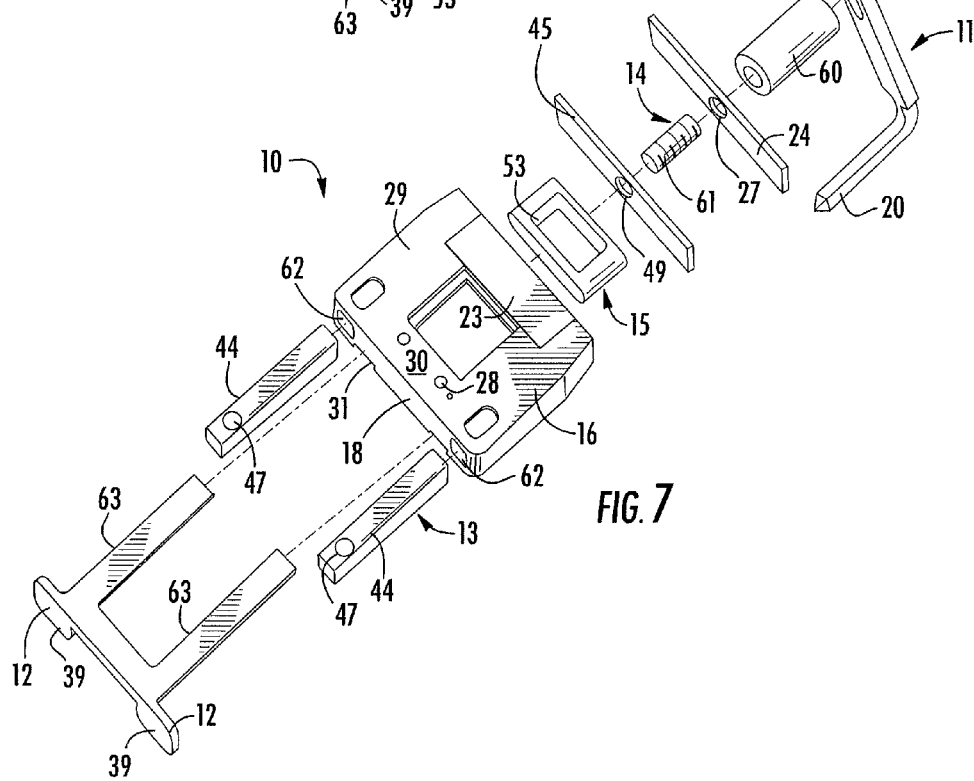

REFERENCE MARK ADJUSTMENT MECHANISM FOR A FEMORAL CALIPER AND METHOD OF USING THE SAME

BACKGROUND OF THE INVENTION

1. Field of the Invention

The present invention is related to methods and apparatuses for knee replacement surgery, and in particular, to methods and apparatuses for sizing femoral components and placing reference marks to facilitate installation of femoral components.

2. Description of Related Art

Performance of a knee replacement surgery typically includes modification of one, or both, of the proximal end of the tibia and the distal end of the femur to have a shape that accommodates the tibial and femoral components, respectively, of the knee prosthesis. Modification typically involves some type of cutting procedure, e.g., with a bone saw, so as to expose, as exemplified by FIG. 15, planar surfaces 100, 101, 102, 103 and 104 on the femur F for attachment of the femoral component 110. An effective attachment of the femoral component 110 to the femur F is facilitated by cutting the femur F at appropriate depths and angles that match the dimensions and angles of the attachment (i.e., non-articulating) surfaces 111, 112, 113, 114 and 115 on the underside of the femoral component 110.

The femur, due to its complex geometry (e.g., lateral and medial condyles and intracondylar notch) can be particularly difficult to shape and therefore benefits greatly from accurate cuts. In addition, proper sizing of the components is important to ensure that the knee prosthesis has adequate stability and range of motion. To this end, various calipers and resection guides have been developed that measure the tibia and femur to determine appropriate sizes for the femoral and tibial components.

The ADVANCE® brand single reference point knee replacement system (Wright Medical, Inc., Arlington, TN) includes a femoral caliper that works off of a single reference point to size the femoral component. The knee replacement system also includes a guide for guiding subsequent cuts to the femur. During femur preparation, first, a starter hole is initiated in the femoral (medullary) canal between the condyles using a drill bit. A fluted intramedullary reamer is inserted into the femoral canal and is turned by hand by grasping and twisting a T-handle end attachment to reduce the occurrence of fat embolisms. An intramedullary alignment rod is then inserted into the reamed hole, preferably at a valgus angle of about 3° or 5°, and becomes the single point from which the remaining cuts are referenced.

A distal femoral resection guide is then assembled onto the intramedullary rod and is placed against the most prominent distal femoral condyle. The resection guide includes slots that are sized to support a bone saw (or other) blade as it cuts a section of the distal femur to form a flat surface in a "distal rough cut." After the initial cut, the distal surface can then be gently planed until flat by a planer that is rotated about the intramedullary rod. The preferred amount of distal resection is between 9 mm and 13 mm.

After planing, the femoral sizing caliper is placed over the intramedullary rod and against the flat, resected distal femur. A pair of feet of the femoral sizing caliper are placed adjacent the posterior portion of the medial and lateral femoral condyles, while a feeler gauge is placed in contact with the anterior cortex of the femur. Movement of the feeler gauge and the feet into position registers a size on a sizing guide of the femoral sizing caliper.

Once the component size has been determined, an anterior-posterior resection guide corresponding to the previously measured size of the femoral component is placed over the intramedullary rod. The anterior-posterior resection guide is moved posteriorly until an anterior feeler gauge of the anterior-posterior resection guide contacts the anterior cortex of the femur. Additional anterior-posterior adjustments can be made using an anterior-posterior positioning screw which moves the resection guide in the anterior-posterior direction in small increments with respect to the feeler gauge. Proper positioning is confirmed by examining the anterior-posterior resection guide to ensure that about 2 mm to 4 mm of posterior condyle is visible under the resection guide.

A locking screw is tightened to secure the anterior-posterior resection guide once it has been positioned as desired and slots defined in the guide are used to complete various other cuts, such as the anterior and posterior chamfer cuts. Additional guides are attached in a similar manner to make other cuts. After all of the cuts have been made, the distal femur has a shape congruent to the attachment surface of the femoral component and the femoral component can be attached to the distal femur.

During this process, a sometimes difficult aspect of femoral component sizing is selecting a size for the femoral component when the femur, which has a natural biological variation in size and morphology from patient to patient, falls in between two sizes. The ADVANCE® brand single reference point knee replacement system generally recommends that a smaller size be selected in such a situation to avoid "overstuffing" the knee in flexion, in other words, to avoid a knee that is too tight and resists full extension. Of course, selecting a smaller size can also result in a somewhat increased laxity of the joint at high knee flexion angles.

In addition to the ADVANCE® Single Reference Point brand knee replacement system, other systems are used for preparing the femur for attachment of a femoral prosthesis. Another single reference point system is described in U.S. Pat. No. 4,474,177 to Whiteside. Also, systems that do not use a single reference point can be employed. For example, there is also an ADVANCE® brand distal cut first knee replacement system that uses an intramedullary rod as a reference point to guide an initial distal cut. However, the remaining surgical steps, such as femoral component sizing and the anterior-posterior cuts, are referenced off of the resected distal femoral surface.

Despite the effectiveness of the above-listed knee replacement systems, additional improvements in systems and methods for preparing the distal femur for attachment of a femoral component are always desirable. Therefore, it would be advantageous to have a femoral caliper that can account for distal femurs that fall in between standard femoral component sizes. For instance, it would be advantageous if the femoral caliper were able to adjust the positioning of the femoral cuts (and hence the position of the femoral implant) to minimize tightness at low flexion angles and laxity at high flexion angles.

BRIEF SUMMARY OF THE INVENTION

The present invention addresses the above needs and achieves other advantages by providing a femoral caliper for facilitating preparation of a femur for installation of a femoral component on the femur.

It is an object of the present invention to provide a femoral caliper capable of providing measurement information and additional options for the sizing of femoral components when the femur falls between femoral component sizes.

It is another object of the present invention to provide a femoral caliper capable of adjusting the positioning of the femoral component to account for the selected femoral component size when the femur falls between femoral component sizes.

These and other objects of the invention are achieved by a femoral caliper having one or more anatomical referencing members for placement against portions of the femur, such as the anterior cortex and posterior portion of the femoral condyles. Advantageously, such positioning allows for measurement of the femur and an indication of the available selection of femoral components. A reference mark positioning guide of the femoral caliper is connected to the anatomical referencing member and is capable of guiding placement of a reference mark on the femur that facilitates positioning of the femoral component. Further advantageously, the femoral caliper includes an adjustment mechanism capable of displacing the reference mark positioning guide relative to the anatomical referencing member in a continuous, non-incremental manner between sizes. This allows adjustment of the position of the reference mark (and hence the femoral component) on the femur to account for the up or down sizing of the femoral component, or other practical and theoretical surgical considerations. Preferably, the adjustment mechanism adjusts the reference mark positioning guide in the anterior-posterior direction to allow balancing of the tightness or laxity of the selected component.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

FIG. 6 is a perspective view of a femoral caliper of another embodiment of the present invention;

FIG. 7 is an exploded view of the femoral caliper of FIG. 6;

DETAILED DESCRIPTION OF THE INVENTION

Figure 1:
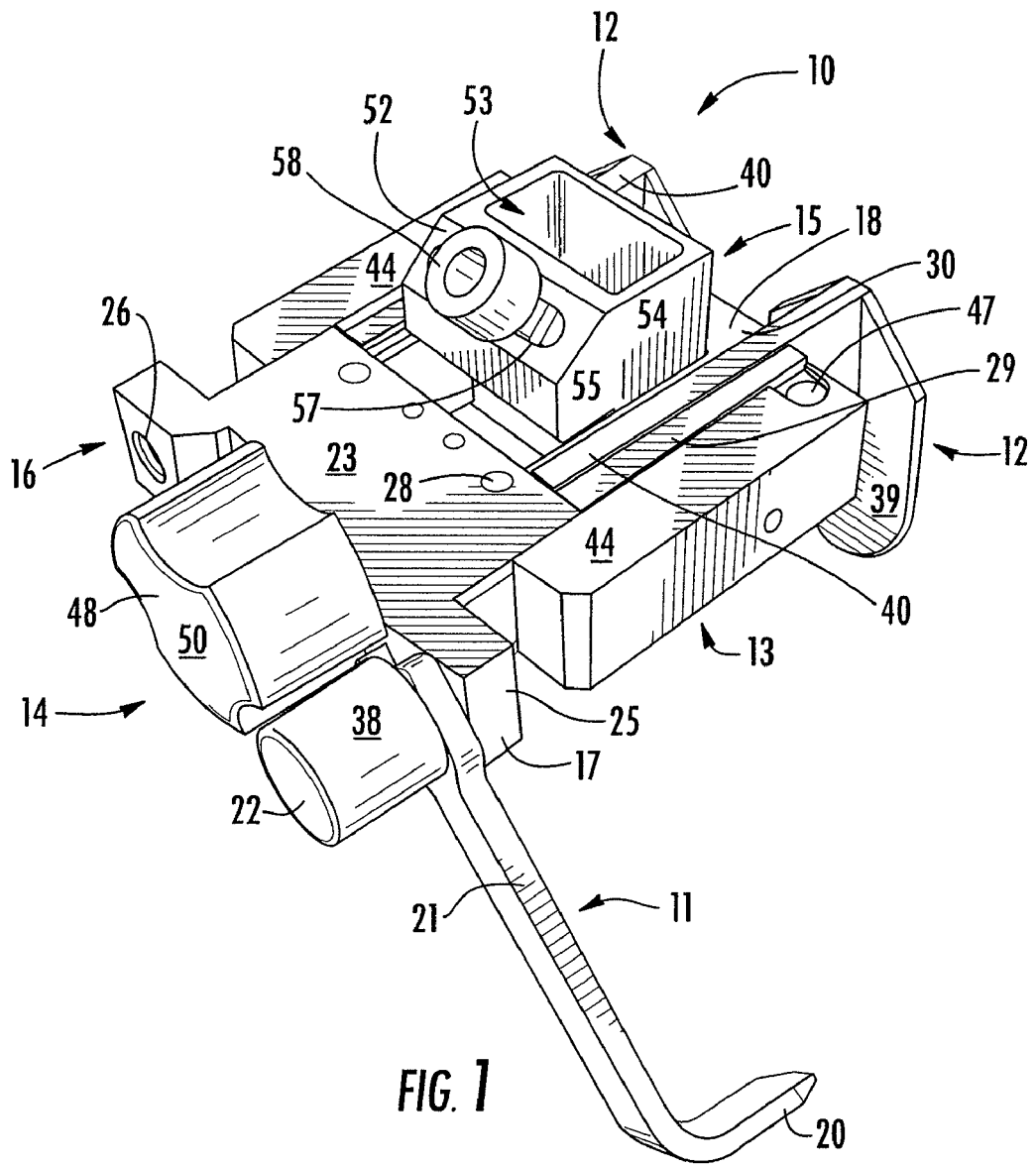
FIG. 1 is a perspective view of a femoral caliper of one embodiment of the present invention.

The present invention now will be described more fully hereinafter with reference to the accompanying drawings, in which some, but not all exemplary embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

The exemplary embodiment of femoral caliper 10 of the present invention includes various anatomical referencing members, including a feeler gauge 11 and a pair of feet 12, a reference mark positioning guide 13, an adjustment mechanism 14, and an intramedullary rod receiver 15 all directly, or indirectly, supported by a support body 16 of the femoral caliper, as shown in FIGS. 1-5.

Figure 3:
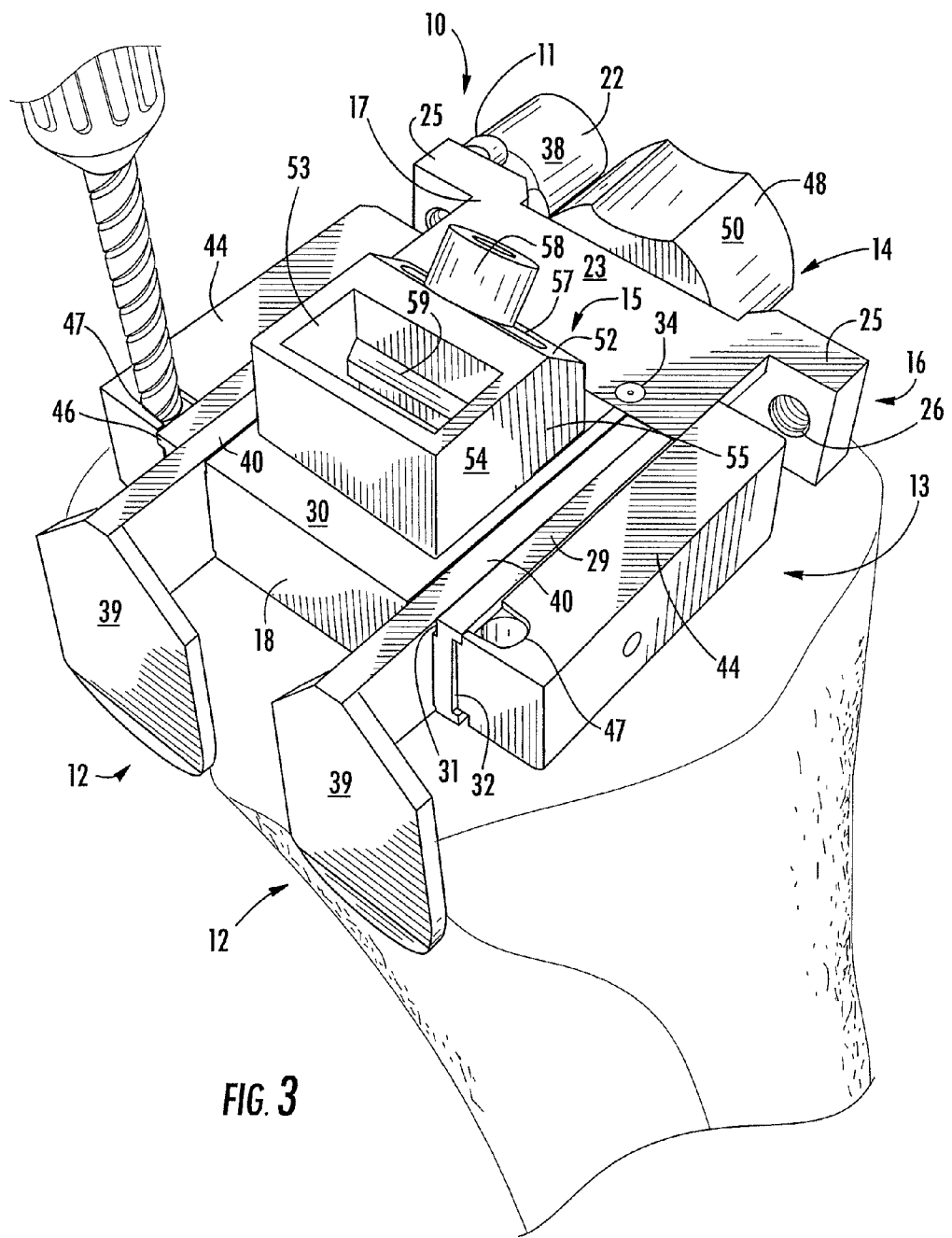
FIG. 3 is another perspective view of the femoral caliper of FIG. 1.
Figure 13:
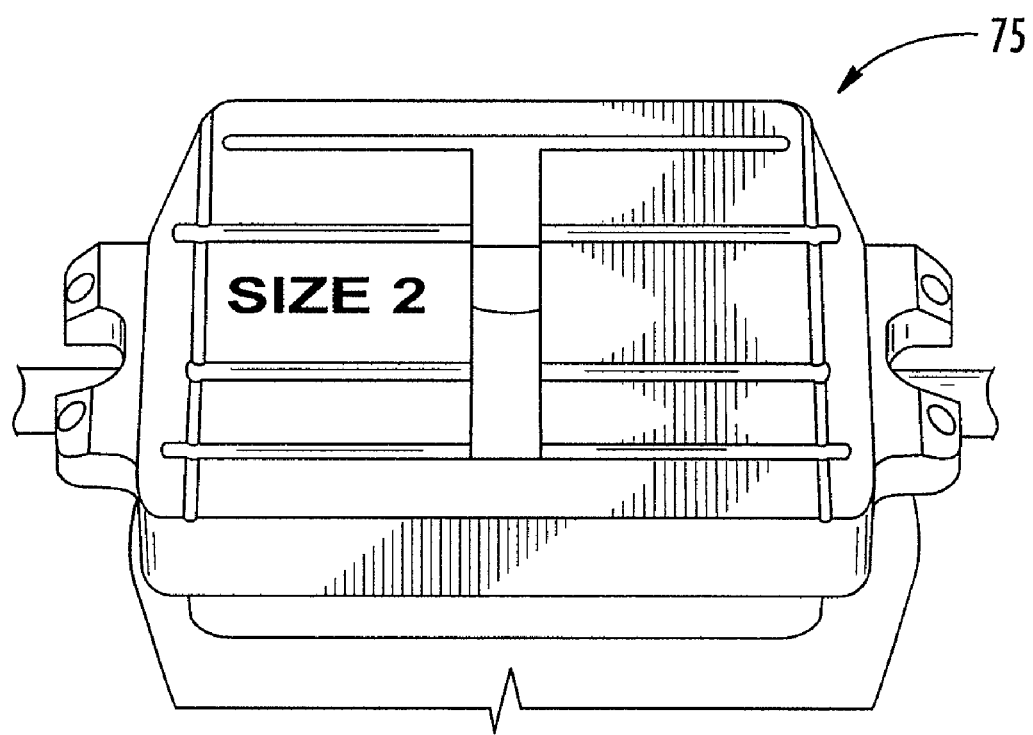
FIG. 13 is a perspective view of an anterior-posterior resection guide positioned using one or more reference marks placed using the femoral caliper of the present invention.

In the invention's most general sense, the femoral caliper 10 is rotationally positioned in a pre-established plane, such as by being positioned over an intramedullary rod 42 extending out of the distal femur via rod receiver 15. Feeler gauge 11 and feet 12 are used to size the distal femur so as to determine what sized femoral component is needed for this particular knee replacement. Then, adjustment mechanism 14 and reference mark positioning guide 13 are used to identify where a reference mark is to be made on the distal femur for positioning of an anterior-posterior resection guide 75, as shown in FIGS. 3 and 13.

Having given a general description of the invention, it will now be described in detail.

Figure 2:
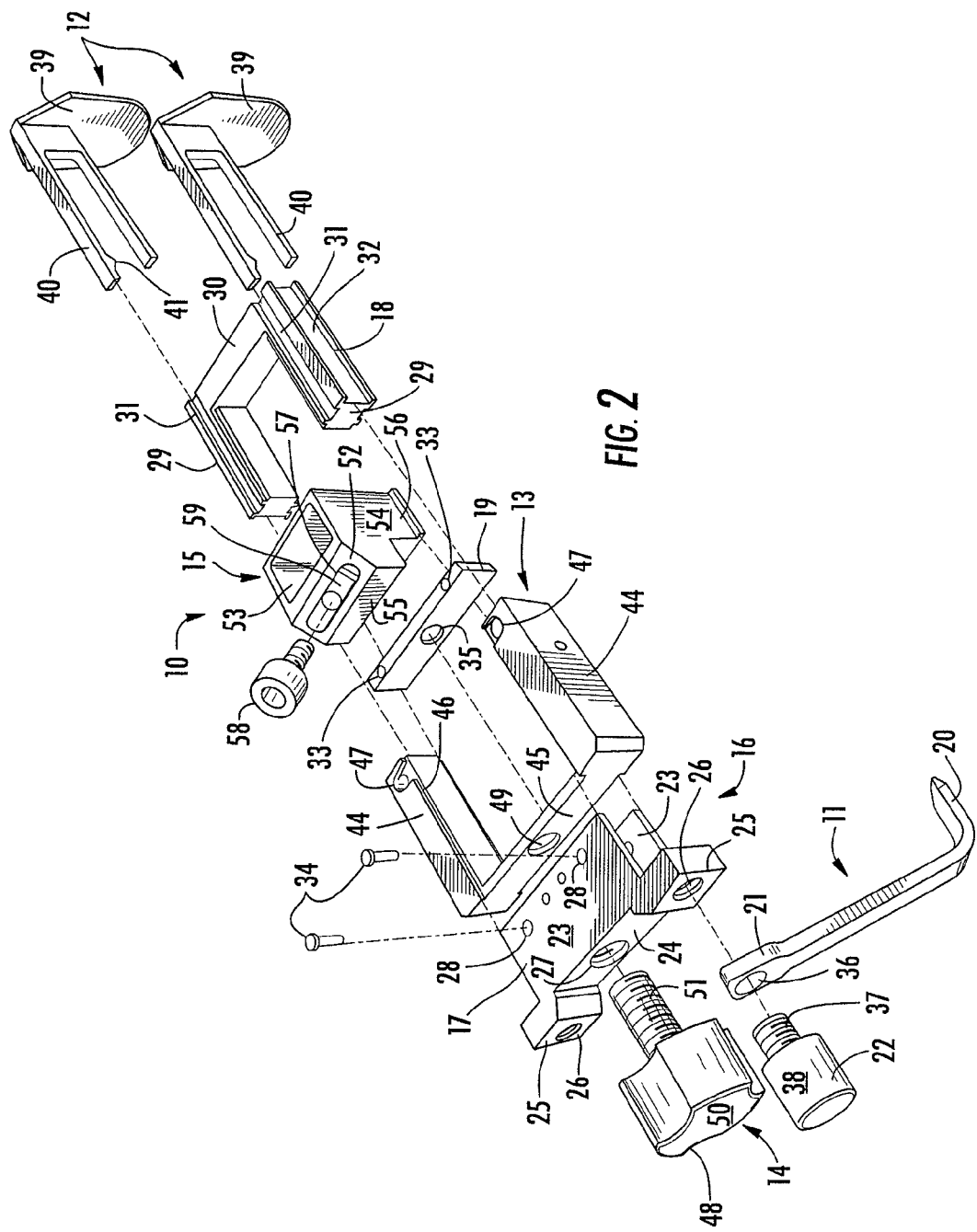
FIG. 2 is an exploded view of the femoral caliper of FIG. 1.

The support body 16 has a generally rectangular shape and includes a feeler support member 17, a foot support member 18 and a stop member 19, as shown in FIG. 2. The feeler support member 17 includes a pair of thin, rectangular walls 23 attached at a base portion 24 and a pair of flanges 25 extending from opposite ends of the base portion 24. Defined in the flanges 25 are threaded openings 26 that, as will be described below, can receive a fastener for supporting the feeler gauge 11. Another opening 27 is defined in the base portion 24 and, as will be described below, is configured to receive a bolt of the adjustment mechanism 14. Additional fastener openings 28 are defined in the rectangular walls 23 of the feeler support member 17.

The foot support member 18 has a U-shape with a pair of arms 29 interconnected at one end by a base 30. Defined on the top and bottom (in the orientation shown in FIG. 2) of each of the arms 29 are a pair of opposing, foot receiving slots 31. A side slot 32 is also defined on the outer side of each of the arms 29 of the foot support member 18. The foot support member is attached to the stop member 19 at the ends of the pair of arms 29, in a conventional manner, such as by fasteners, welding, etc.

The stop member 19 has a rectangular shape that is fitted to extend between the walls 23 of the feeler support member 17 and includes a pair of fastener openings 33 defined through its top and bottom edges and positioned to correspond to the fastener openings 28 of the feeler support member. In this manner, fasteners 34 (e.g., rivets or screws) can pass through the overlapping openings to attach the stop member 19 and the foot support member 18 to the feeler support member 17, as shown in FIG. 1. Also defined in the stop member 19 is an opening 35 between its front and back surfaces that is sized to receive a bolt of the adjustment mechanism 14.

Figure 8:
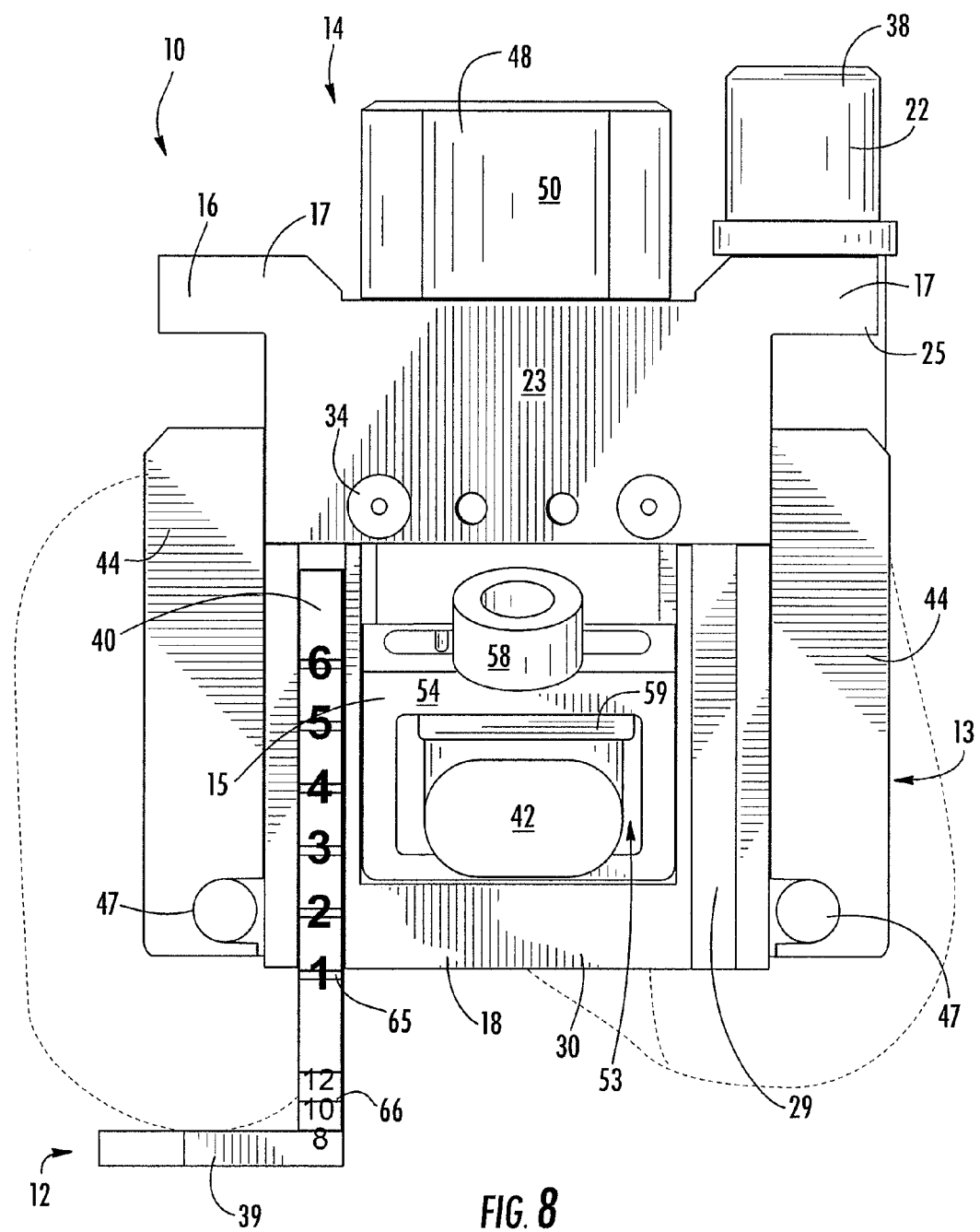
FIG. 8 is a plan view of a femoral caliper of another embodiment of the present invention including posterior cut indicia.

In general, the rod receiver 15 has a rectangular box shaped body 54 and a flange 55 extending from one end of the body, as shown in FIGS. 1-5. The body 54 defines a rod opening 53 extending therethrough between two opposite surfaces and having a rectangular cross-section. The rectangular cross-section is preferably matched to the cross-section of the intramedullary rod 42 to be used with the femoral caliper 10, as shown in FIG. 8. Defined on lateral sides of the body 54 are a pair of channels 56 that are configured to engage, and slide along, the inside lateral edges of the arms 29 of the foot support member, as shown in FIG. 2.

Figure 4:
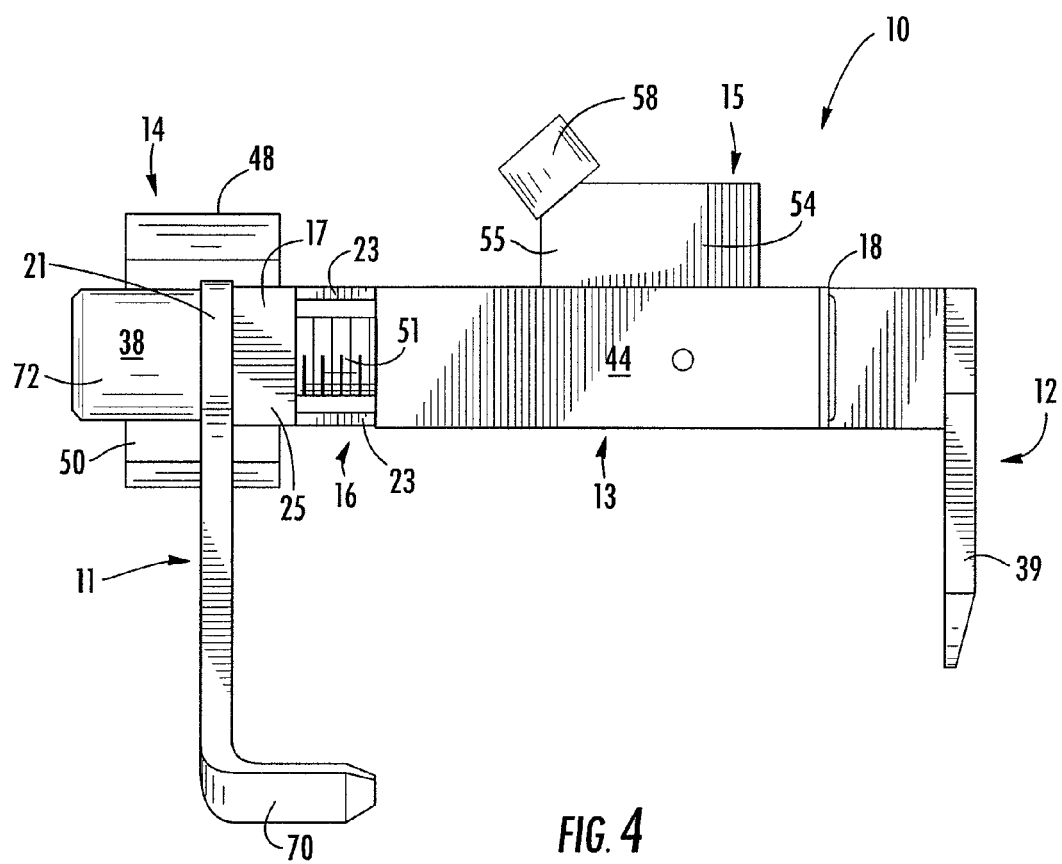
FIG. 4 is a side elevation view of the femoral caliper of FIG. 1.
Figure 5:
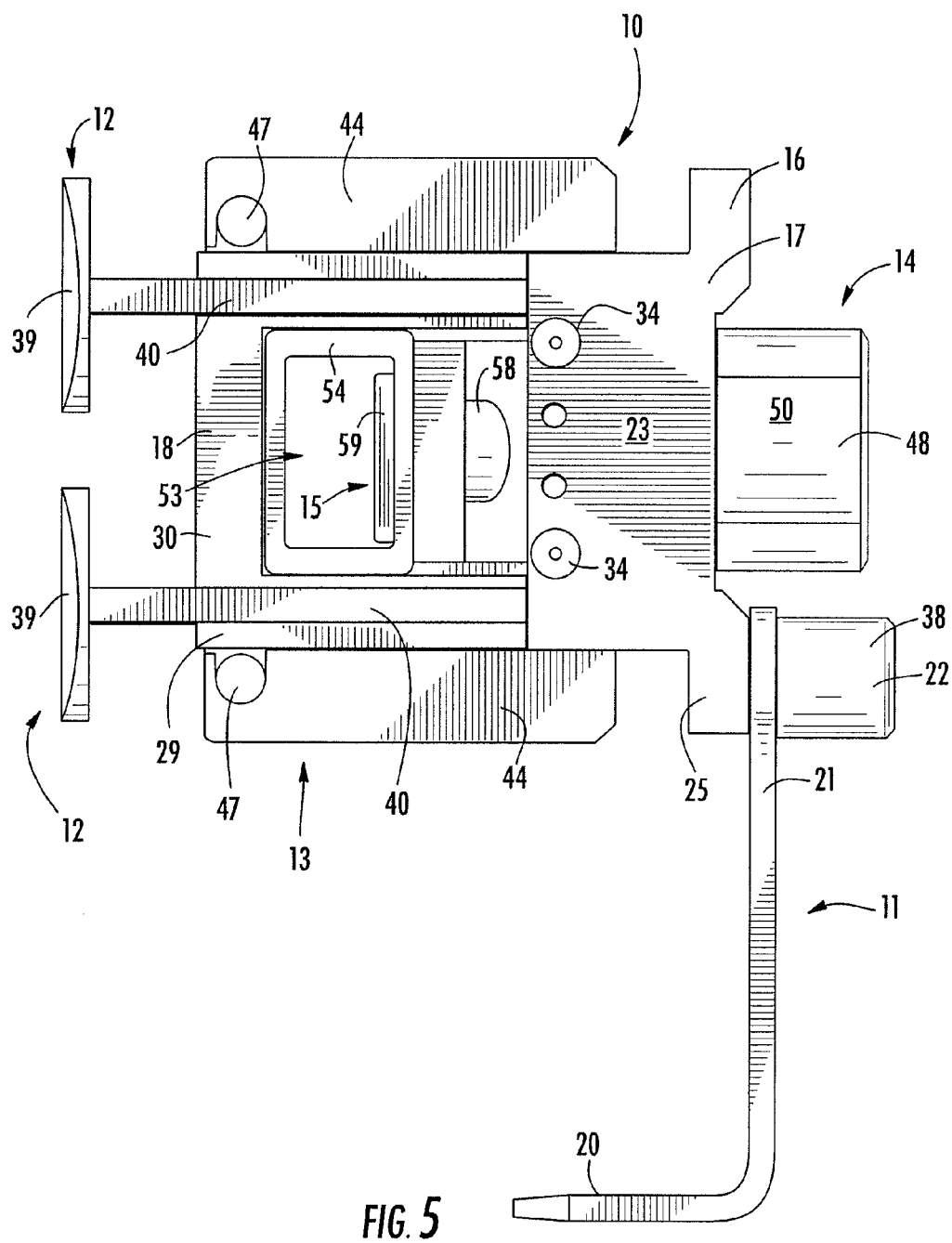
FIG. 5 is a plan view of the femoral caliper of FIG. 1.

The flange 55 defines a lock screw slot 57 that extends between an external, beveled face 52 at one end and the rod opening 53 at the other end. Extending through the lock screw slot 57 is a lock screw 58 that has a head which abuts the beveled face 52 and a threaded portion that extends through the lock screw slot. The threaded portion engages an interference member 59 and when turned can advance or retract the interference member into the rod opening 53, as shown in FIGS. 3 and 4.

When advanced, the interference member 59 can engage the intramedullary rod 42 so as to inhibit sliding of the rod receiver 15 along the rod. The rectangular shape of the rod opening 53 and its close fit around the similarly rectangular intramedullary rod 42 inhibits rotation with respect to the intramedullary rod 42 and the femur. As mentioned above, the pair of channels 56 are configured to engage, and slide along, the inside lateral edges of the arms 29 of the foot support member. Therefore, once the intramedullary rod 42 is engaged by the rod receiver 15 and locked thereto, only anterior-posterior translation of the support body 16 with respect to the intramedullary rod 42 is permitted, allowing adjustment of the feeler gauge 11 and feet 12 to measure the femur and size the femoral component as is described below. As a result, the rotation of the femoral caliper 10 is fixed by its attachment to the intramedullary rod 42. The feeler gauge 11 has an elongate, L-shape with a pair of opposite ends, including a free end 20 and a fixed end 21 opposite the free end, as shown in FIG. 2. The fixed end is widened slightly to have a rectangular shape and defines a circular opening 36 for receiving a feeler gauge fastener 22. The free end 20 extends at a right angle from the fixed end 21 of the feeler gauge 11 and is directed toward the support body 16 of the femoral caliper 10 and the pair of feet 12 on the opposite side of the support body.

The feeler gauge fastener includes a threaded end 37 and a cylindrical head 38 wherein the threaded end can be extended through the circular opening 36 of the feeler gauge 11 and one of the threaded openings 26 of the flanges 25 and hand-tightened using the cylindrical head. In this manner, the feeler gauge 11 can be attached to either of the flanges 25 and its orientation adjusted so that the free end 20 touches the anterior cortical bone on right and left femurs of varying sizes and shapes prior to hand-tightening of the of the feeler gauge fastener 22.

Each of the feet 12 includes a paddle 39 and a pair of spaced prongs 41, as shown in FIG. 2. The paddle 39 is constructed of a relatively thin sheet of material having one rounded edge configured to extend over a rear portion of a respective one of the femoral condyles during sizing. The spaced prongs 41 are fixed at a common base portion in a position centered between two lateral edges and adjacent a top edge of the paddle 39. The prongs 41 extend outward from the paddle 39 and are sized to fit within the foot receiving slots 31 on opposite sides of the arms 29 of the foot support member 18. The spacing of the prongs 41 is such that they snugly grip the arms 29 of the foot support member 18. Optionally, one or more of the prongs 41 may include a tooth 41 that extends toward the opposite prong and tightens the fit of the prongs over the arms 29 by causing a slight cantilever bend in the prong.

The prongs 40 may also include sizing indicia 65 (e.g., six hash marks with associated size numbers corresponding to six standard femoral component sizes) that extend along the outside surface of the prong, as shown in FIG. 8. Sliding of the feet 12, and in particular the prongs 40 within the foot receiving slots 31, changes the position of the sizing indicia 65 relative to a landmark on the support body 15 (such as the posterior edge of the support body) when the paddles 39 of the feet are adjusted to abut the posterior surfaces of the femoral condyles. As a result, positioning of the free end 20 feeler gauge 11 against anterior cortical bone of the femur and the feet 12 against the posterior surfaces of the femoral condyles registers a size via the sizing indicia 65. In some instances, however, the landmark on the support body 15 falls in between the hash marks on the prong.

It should be noted that other methods and/or structure may be used to measure the femur for sizing the femoral component and still be within the scope of the present invention. For instance, alternatives to the feeler gauge 11 and feet 12 as referencing members may simply include a device having indicia that can be positioned at the anterior-most edge of the flat distal femoral surface, thereby allowing measurement of the anterior-posterior depth of the femur. As another example, the feet 12 could be replaced with another feeler gauge, or different structure that is displaceable relative to the feeler gauge 11, that can contact a desired anatomical reference point on the femur. Notably, these anatomical reference points may differ depending upon the preferences of the surgeon, recent advances in surgery, modifications of the femoral component, etc. Similarly, the feeler gauge could be replaced with some other type of referencing member.

The referencing members could also measure other aspects beyond the anterior-posterior depth, such as curvature of the condyles or width of the of the femur, which can be used to correlate femoral component sizes. Regardless of what portion or portions of the femur are measured, however, it is anticipated that femur sizes will sometimes not closely match the femoral component as long as standard or discrete femoral components are used in knee replacement surgery. To accommodate such cases, the present invention advantageously can combine sizing of the component with additional adjustability to reposition reference marks for femoral component placement, thereby allowing adjustment of the tightness or laxity of the selected knee component with a single device.

The reference mark positioning guide 13 has a U-shape and includes a pair of arms 44 attached at one end by a base portion 45, as shown in FIG. 2. The pair of arms have a generally rectangular cross-section except for defining a pair of edge slots 46 that extend along their interior, top and bottom corners. These slots are sized to engage corresponding edges defining the side slot 32 on each of the arms 29 of the foot support member 18 so that the foot support member and reference mark positioning guide can slide relative to each other in the anterior-posterior direction (or other direction depending upon the orientation of the femoral caliper 10).

The base portion 45 is sized to extend and slide between the opposing walls 23 of the feeler support member 17. In addition, lateral edges of the opposing walls 23 extend into the edge slots 46 of the pair of arms 44. In this manner, the reference mark positioning guide 13 is free to stably slide (preferably in one translational degree-of-freedom) with respect to the various anatomical referencing members. The range of sliding motion of the base portion 45 is inhibited at one end by the base portion 24 of the feeler support member 17 and at the other end by the stop member 19. Defined in the base portion 45 is a threaded opening 49 which is coincident with the opening 35 defined in the stop member 19 of the support body 16.

At the free ends of the arms 44 opposite the base portion 45 are defined a pair of drill guide openings 47 that extend through the arms in a generally proximal-distal direction when the femoral caliper 10 is positioned on the planed distal surface of the femur. The drill guide openings 47 are sized to receive drill bits that are themselves sized to cut holes into the distal femur surface (as shown in FIG. 3) for receiving a pair of positioning pegs extending from the anterior-posterior resection guide 75. These positioning pegs determine the positioning of the resections and, in turn, therefore determine the positioning of the femoral component.

It should be noted that reference marks can be cut, marked or otherwise noted on the femur in other ways than through the use of a drill and drill guide openings 47 and still be within the scope of the present invention. For instance, the reference mark positioning guide 13 might include pegs that can be hammered or pushed into the femur, or may provide for guide markings, edges or openings for facilitating marking with ink or dyes, or radio-opaque substances or markers.

The adjustment mechanism 14 may include a rotary member such as an adjustment screw or bolt 48 having a knob 50 at one end of a partially threaded shaft 51, as shown in FIG. 2. The shaft 51 of the bolt extends through the opening 27 (which is not threaded) defined in the feeler support member 17 of the support body 16, the threaded opening 49 defined in the base portion 45 of the reference mark positioning guide 13 and the opening 35 in the stop member 19 (which is also not threaded). The knob of the bolt 48 abuts the outside surface of the feeler support member 17.

Because the opening 27 in the feeler support member 17 and the opening 35 of stop member 19 the support body 16 are not threaded, the bolt 48 rotates freely therein. Right handed rotation of the bolt 48 in the threaded opening 49, however, draws the base portion 45, and therefore the reference mark positioning guide 13, along its threaded shaft toward the knob 50 of the bolt. Left handed rotation, conversely, advances the base portion 45 away from the knob 50 of the bolt 48. Of course these directions could be varied by changing the handedness of the threads.

Preferably, unthreaded portions of the shaft 51 of the bolt near the knob 50 and at its free end have an outer diameter that is less than that of the threaded portions therebetween. In this manner, the shaft 51 of the bolt 48 cannot translate with respect to the support body 16 which supports the feeler gauge 11 and the feet 12. As a result, the single degree-of-freedom translating motion of the reference mark positioning guide 13 occurs with respect to the bolt 48, the support body 16, the feeler gauge 11 and the feet 12. This allows adjustment of the anterior-posterior positioning of the drill guide openings 17 on the distal femur subsequent to measurement of the femur to size the femoral component.

It should be noted that the adjustment mechanism 14 of the present invention need not be limited to the above-described structure and can include different structure that is capable of moving the reference mark positioning guide 13 with respect to one or more anatomical referencing members. For instance, the adjustment bolt 48 could be replaced with a sliding mechanism, a rack and pinion, a ratchet or other structure that allows controlled translation or other motion of the reference mark positioning guide 13 in one or more degrees-of-freedom. Additional, or different, degrees of freedom may be controlled by other embodiments of the femoral caliper 10 of the present invention depending upon other research findings or opinions indicating that replacement joint performance can be improved with different changes in position and orientation (e.g., a change in varus-valgus angulation).

Preferably, the adjustment mechanism 14 is configured for finer movement than the movement of the feeler gauge 11 and the feet 12. To this end, the adjustment mechanism can be configured to have a maximum displacement that is less than a maximum relative displacement between the feeler gauge and the feet. For cases in which adjustment of the reference mark positioning guide 13 is primarily directed to compensating for femur sizes that fall between standard component sizes, the maximum displacement of the adjustment mechanism 14 is preferably at least equal to the maximum relative displacement between the feeler gauge and the feet when moving from one component size position to another adjacent component size position.

Also, it should be noted that the adjustment mechanism 14 could be considered to include various parts of the support body 16, the reference mark positioning guide 13 and other structure of the femoral caliper 10 that facilitate the adjustable motion of the drill guide openings 47 (or other guides for guiding reference mark positioning), such as the various members of the support body and the openings defined therein. Preferably, the femoral caliper 10 is constructed of a material of sufficient rigidity to ensure accurate measurement of the femur and guiding of the drill bit for placing reference marks such as stainless steel or titanium. However, the femoral caliper of the present invention should not be considered limited to any particular material or combination of materials.

As described above and below, rotation of the femoral caliper 10 is typically fixed with respect to the intramedullary rod 42. Therefore, prior to use of the femoral caliper the intramedullary rod 42 is inserted into the medullary canal of the femur and its rotation can be determined using one or more techniques. For instance, rotation of the intramedullary rod 42 may be determined visually by the healthcare worker, via a sulcus clamp that slides over the intramedullary rod and grips an anterior and posterior portion of the femur between the condyles or by using a crosshair having a pair of hand grips extending at right angles to each other that meet at, and are attached to, the intramedullary rod. Another example of a rotational alignment technique includes an intramedullary alignment guide having a guide handle which is illustrated in FIGS. 3 and 4 of U.S. Pat. No. 4,474,177 which is hereby incorporated in its entirety herein by reference. These, and other, techniques for determining rotation of the intramedullary rod are outside the scope of the present invention and are therefore not illustrated in detail herein.

After rotation of the intramedullary rod 42 is determined, a distal resection guide is fixed to the inramedullary rod, the distal rough cut is made and then the surface is smoothed using a planer. An exemplary distal cutting guide and planer are illustrated in FIGS. 19 and 20 of U.S. Pat. No. 4,474,177. Beyond the above-described techniques for preparing the femur and setting rotation of the intramedullary rod 42, the present invention should not be considered limited to use with the intramedullary rod or as necessitating any particular preparation of the femur, such as the use of an initial distal cut. However, setting the rotation of the intramedullary rod 42 and making the distal cut prior to use of the femoral caliper 10 is generally preferred and one method of using the femoral caliper 10 with the intramedullary rod and distal cut is therefore described below.

During use, the femoral caliper 10 of the present invention allows measurement of the femur for femoral component sizing combined with the ability to adjust the position of reference marks used to position the femoral component. Once the intramedullary rod 42 has been inserted into the femoral canal and the distal end of the femur has been planed, the rectangular rod opening 53 of the rod receiver 15 is slipped over the intramedullary rod 42. The femoral caliper 10 is slid down the rod until its support body 16 is adjacent the planed distal end of the femur. The lock screw 58 of the rod receiver 15 is advanced to press the interference member 59 against the intramedullary rod 42 and, in combination with the rectangular cross-section of the rod and rod opening 53, proximal-distal translation and all axes of rotation of the femoral caliper 10 are inhibited.

The free end 20 of the feeler gauge 11 is then placed against the anterior femoral cortex and the feet 12 are adjusted until the paddles 39 abut the posterior edges of the femur. Such adjustment changes the relative positioning of the sizing indicia on the prong 40 of one, or both, of the feet 12 with respect to the support body 16, thereby registering a femoral component size. If the sizing is indeterminate (i.e., somewhere in between two of the component sizes), or if desired for surgical theory purposes, the reference mark positioning guide 13 can then be adjusted or readjusted. Preferably, if different measurements are registered by independent feet 12, the smaller component size is used to avoid overstuffing the knee.

In particular, the knob 50 of the of the adjustment bolt 48 can be turned within the threaded opening 49 defined in the base portion 45 of the reference mark positioning guide 13 to advance, or retract, the reference mark positioning guide along the side slots 32 defined by the arms 29 of the foot support member 18. In the orientation of the illustrated embodiments, this translation is in the anterior-posterior direction. Once the drill guide openings 47 on the arms 44 of the reference mark positioning guide 13 are desirably positioned on the distal femur, a drill bit is inserted into each of the drill guide openings 47. Drilling with the bit places the reference mark holes on the femur which are later used to position the anterior-posterior resection guide 75 for subsequent cuts to the femur, as shown in FIG. 13. Generally, the reference marks are placed more posterior for smaller femoral components (to reduce laxity) and more anterior on larger components to avoid "over stuffing" the knee.

Another embodiment of the femoral caliper 10 of the present invention is shown in FIGS. 6 and 7. In this embodiment, an adjustment cylinder 60 allows in-line, combined adjustment of the position of the reference mark positioning guide 13 as well as the feeler gauge 11. In particular, the adjustment cylinder has a threaded opening at each end. At one end, the threaded opening receives the feeler gauge fastener 22 and at its other end a length of threaded rod 61 that turns with the adjustment cylinder 60 to urge the reference mark positioning guide 13 in the anterior-posterior direction. Other variations illustrated by the embodiment of FIGS. 6 and 7 include openings defined within the body 16 to allow slidable housing of the pair of arms 44 of the reference mark positioning guide 13. Instead of prongs 40, the feet 12 include thin legs 63 that slide into a pair of foot receiving slots 31 defined on the foot support member 18.

In another embodiment, the femoral caliper 10 of the present invention can include a top plate 64 that can be affixed to the reference mark positioning guide 13 so as to further facilitate relatively fine adjustments of the drill holes, or other reference marks, used to attach various femoral cutting guides, as shown in FIGS. 8-12. In this embodiment, each paddle 39 of the femoral caliper 10 also includes posterior cut indicia 66 that indicate the amount of bone to be removed from the posterior of the condyles depending upon the positioning of the reference mark positioning guide 13 using the adjustment mechanism 14, as shown in FIG. 8.

Figure 9:
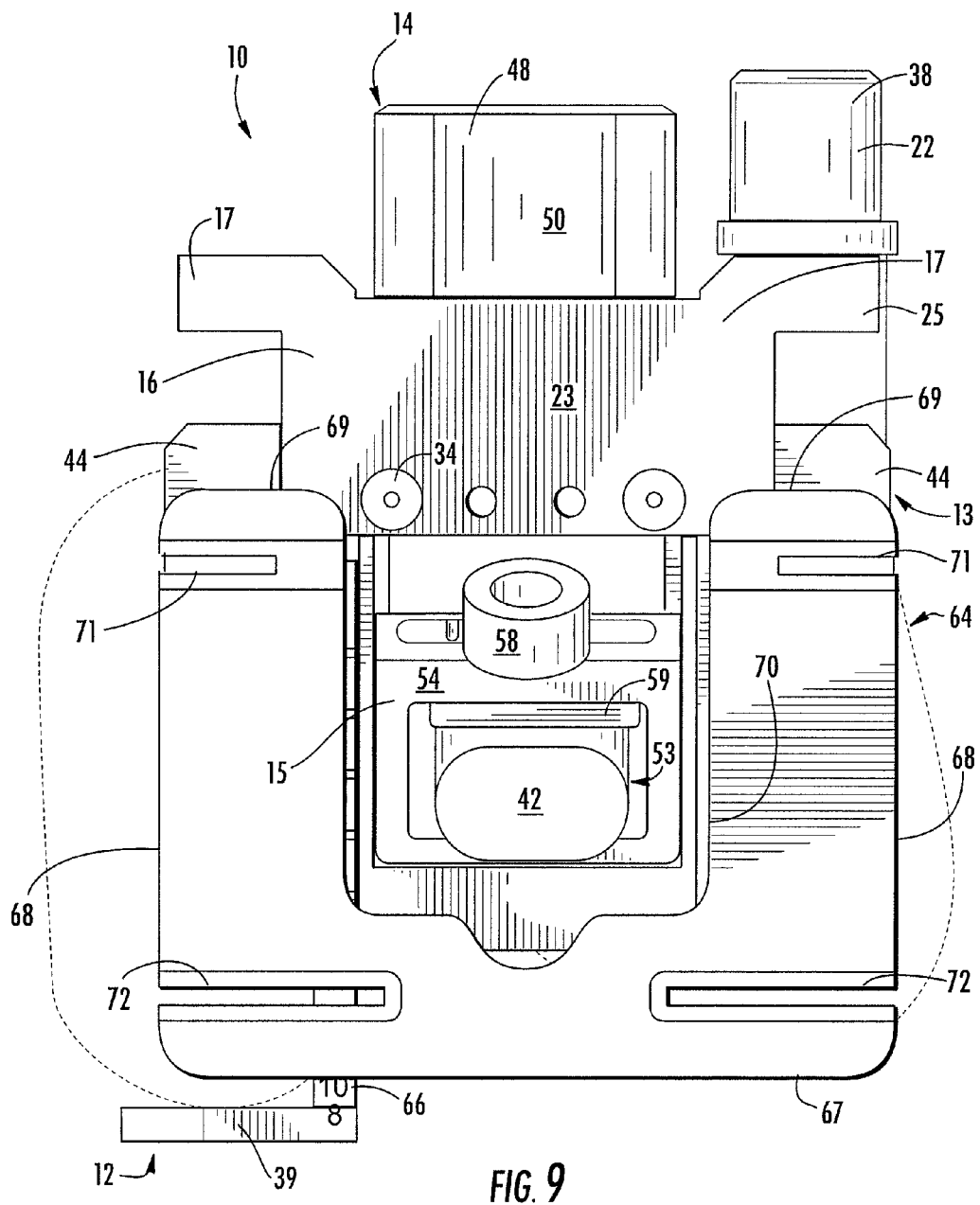
FIG. 9 is a plan view of the femoral caliper of FIG. 8 including a top plate for referencing an amount of posterior cut.
Figure 10:
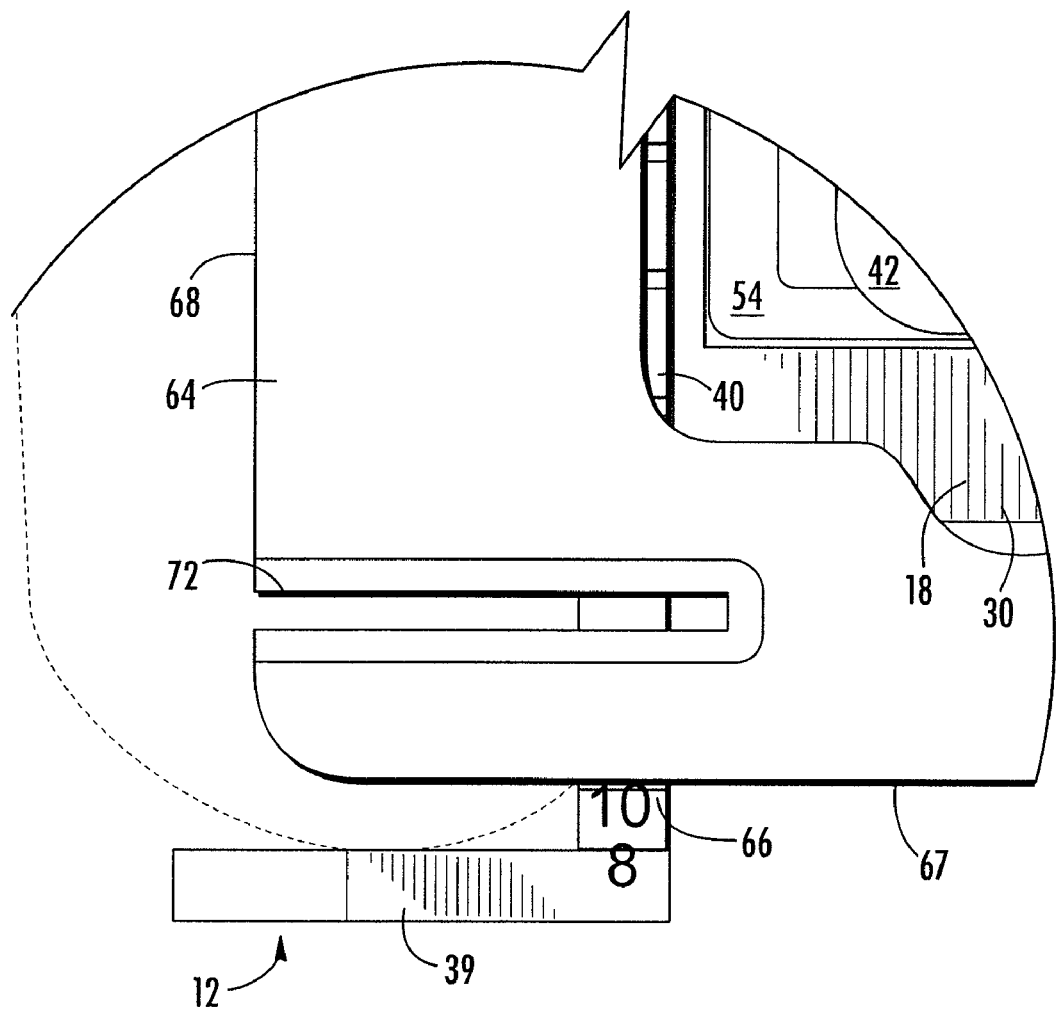
FIG. 10 is an enlarged view of the posterior cut indicia and top plate of FIG. 8.

The top plate 64 generally has a rectangular shape with a posterior edge 67, a pair of lateral edges 68 and an anterior edge 69, as shown in FIG. 9. Defined in the top plate is a rectangular opening 70 that extends posteriorly from the anterior edge and is sized to allow the top plate 64 to extend around the rod receiver 15 when attached to the reference mark positioning guide 13. Also defined in the top plate 64 are reference guide slots, including two anterior guide slots 71 positioned near, and extending parallel to, the anterior edge 69 and two posterior guide slots 72 positioned near, and extending parallel to, the posterior edge 67.

Figure 11:
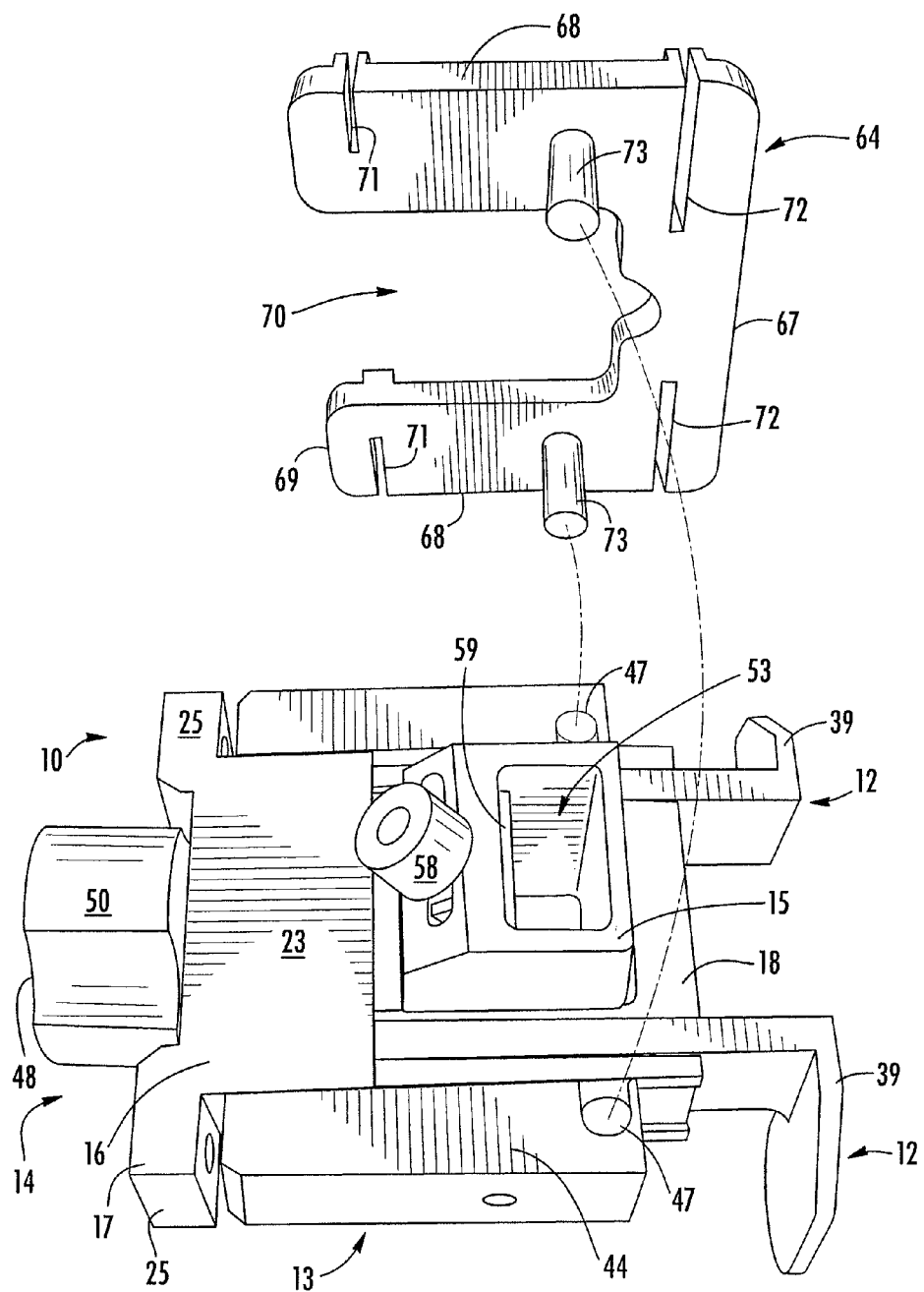
FIG. 11 is an exploded view showing detachment of the top plate of the femoral caliper of FIG. 8.

On its underside, the top plate 64 includes a pair of fixation pegs 73 sized and positioned to be extendable into the drill guide openings 47 defined in the reference mark positioning guide 13, as shown in FIG. 11. In this manner, the top plate 64 can be fixed to, and its position adjusted with, movement of the reference mark positioning guide 13, as shown in FIG. 9.

Several sizes of top plate 64 are preferably available during surgery, each size corresponding with a selected one of the discrete sizes of femoral component initially determined by adjusting the feet 12 of the femoral caliper. Preferably, the sizing plate corresponding to the sizing indicia 65 is used if the measurement is relatively close to the hash mark indicating the size. If the measurement falls between the hash marks (i.e., between two sizes), then preferably the smaller sized top plate 64 is used, corresponding to the smaller sized femoral component.

Figure 12:
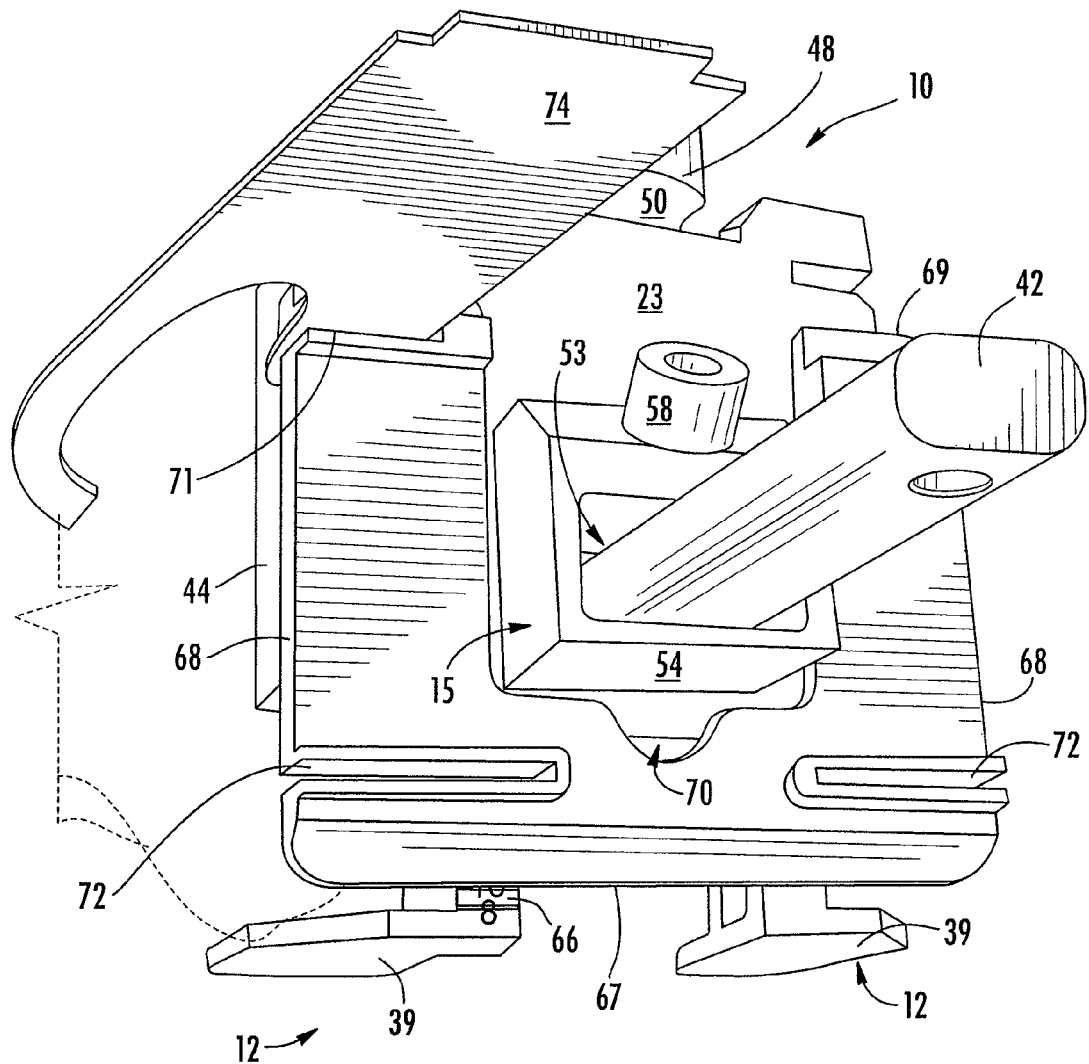
FIG. 12 is a perspective view of the femoral caliper of FIG. 8 including an angel wing gauge.

The top plate 64 is configured to allow visualization and measurement of the cuts to be made to the femur to fit its respective one of the femoral components. In particular, the posterior edge 67 is configured to indicate the amount of posterior condylar resection by overlying the posterior cut indicia 66 on each paddle 39, as shown in FIG. 12. Because the top plate 64 changes position with the anterior-posterior adjustability of the reference mark positioning guide 13, the amount of posterior cut can be adjusted. Preferably, due to the constant center of rotation desired for most femoral components, the amount of posterior cut is about equal to, or slightly larger, than the amount of distal cut. For example, in the embodiment illustrated in FIG. 12, the 10 mm posterior cut corresponds to a 9 mm distal cut.

Alignment of the anterior and posterior cuts can be visually confirmed by looking through the anterior and posterior guide slots 71, 72 which correspond to the anterior and posterior cut positions. Visualization of the resection may also be aided by the use of an angel wing caliper 74 placed in one of the guide slots 71, 72, such as one of the anterior guide slots, as shown in FIG. 12. Once the proper positioning of the reference mark positioning guide 13 has been confirmed, the holes are drilled in the femur via the drill guide openings 47 for attachment of the anterior-posterior resection guide 75, as shown in FIG. 13.

Figure 14:
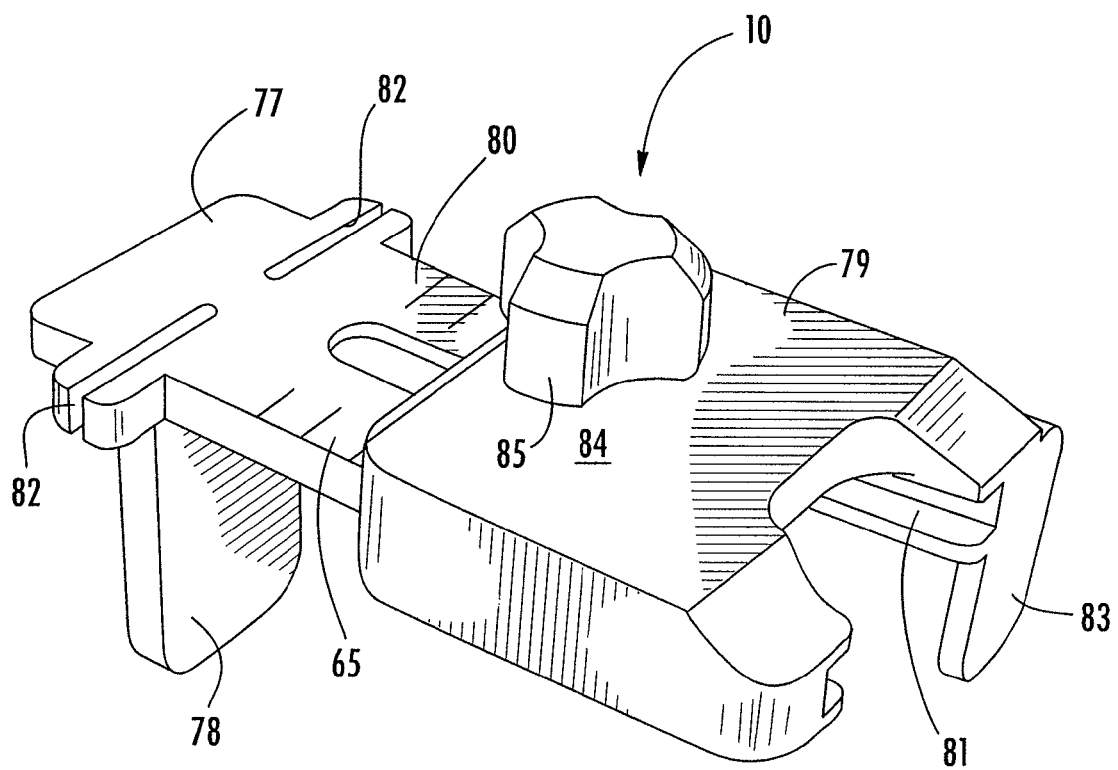
FIG. 14 is a perspective view of a femoral caliper of another embodiment of the present invention that employs anterior cuts to reposition a femoral component.
Figure 15:
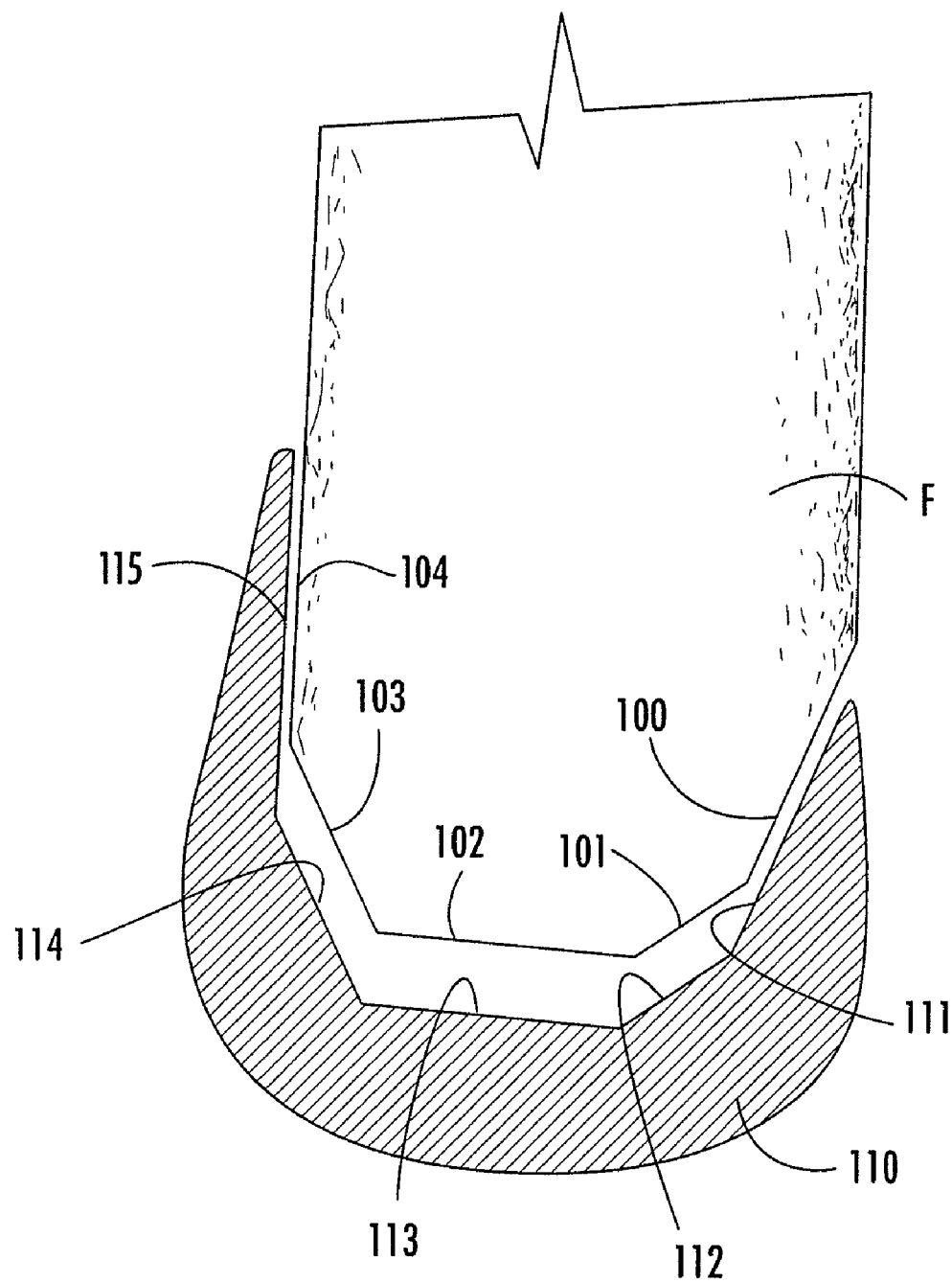
FIG. 15 is a sectional view of a distal femur and femoral component of the prior art.

In yet another embodiment of the present invention, the femoral caliper 10 is configured to reference off of an anterior rough cut, as shown in FIG. 14. In this embodiment, the femoral caliper includes an anterior cutting guide 77 that is slidably mounted within a posterior landmark referencing member 79. The anterior cutting guide 77 includes a broad anterior paddle 78 and a slidable member 80. The anterior paddle 78 extends from the slidable member 80 at a right angle. The slidable member is sized to fit within a pair of opposing channels 81 defined in the posterior landmark referencing member 79. Also, the slidable member 80 defines a pair of anterior cutting guide slots 82 positioned slightly posterior to the anterior paddle 78. Sizing indicia 65 are positioned on a top surface of the slidable member 80.

The posterior landmark referencing member 79 includes its own, relatively smaller posterior paddle 83, a main body 84 and a locking bolt 85. The posterior paddle 83 is positioned opposite the anterior paddle 78 and is sized to abut the posterior of one of the condyles. The posterior paddle 83 is attached to, and extends away from the main body 84 at about a right angle. Defined in the main body are the above-described channels 81 that are sized to slidably receive the slidable member 80. The locking bolt 85 extends through a threaded opening in the middle portion of a top surface of the main body 84. One end of the locking bolt 85 includes a knob for rotary motion and turning the bolt advances its other end into contact with the slidable member 80.

Prior to use of the femoral caliper 10 shown in FIG. 14, an anterior rough cut is made to the femur to establish an initial flat anterior plane. The anterior paddle 78 is positioned against the flat anterior plane (thereby locking the rotational position of the caliper 10) and the members 79, 80 are brought together until the posterior paddle 83 abuts one of the posterior condyles. At this point, the anterior edge of the main body 84 indicates a size of the femoral component by extending over the indicia 64 on the slidable member 80. If the caliper 10 registers near a size, the caliper is removed and further cutting guides are used to prepare for that sized femoral component.

In a case where the measurement is in between sizes, the locking bolt 85 can be locked to secure the femoral caliper 10 to the femur and then an anterior cut made using the slots 82 removing 2 mm of anterior bone. Then, the locking bolt 85 is loosened and the anterior cutting guide 77 is advanced further into the posterior landmark referencing member 79. Locking, cutting and unlocking can be repeated until a desired amount of additional femoral bone has been resected in 2 mm increments. The remaining cuts to the femur are then made off of this anterior reference cut. As a result, the femoral component position has been moved posteriorly to adjust for using the smaller femoral component. It should be noted that larger or smaller increments of cut could be used with varied positioning and width of the anterior cutting guide slots 82.

Preferably the anterior paddle is fairly broad so as to effectively lock out rotation of the caliper 10 while the cuts and measurements are being made. For instance, the anterior paddle 78 could be greater than ⅜, ¾ to 1 or more inches (depending on the size of the femur) and span over 15% or 25% the width of the femur and prevent rotation. Other anterior members could also be used that are not necessarily "paddle" shaped, such as two pegs or multiple rigid surfaces that span such widths and effectively lock out the rotation of the caliper 10 a sufficient amount to allow stable cutting and/or measurement.

The femoral caliper 10 of the present invention has many advantages. For instance, the femoral caliper can allow for additional adjustment of the positioning of a femoral component in combination with measurement of the femoral component. This is particularly useful to avoid "over stuffing" and other problems that might be encountered when the femur cannot be exactly matched to a standard femoral component size. For instance, the anterior-posterior positioning of reference marks to be used for placing the femoral component may be adjusted to account for under or oversized femoral components. Use of the adjustment bolt 48 facilitates such adjustment with an easy, hand-controlled motion. The stop member 19 at one end, and the base portion 24 of the feeler support member 17 provide end points for the amount of readjustment. In addition, the support body 16 itself is configured, such as with the use of the walls 23 of the feeler support member 17, to allow stable sliding movement.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A femoral caliper for preparing a femur for installation of a femoral component on the femur, said femoral caliper comprising:
   a reference mark positioning guide configured to be juxtaposed with a planed distal surface of a femur and capable of guiding placement of at least one reference mark on the planed distal surface of the femur, said reference mark on the femur facilitating positioning of the femoral component;
   a first anatomical reference member comprising a pair of paddles, each paddle configured to abut the posterior surface of a femoral condyle and being moveable in the anterior-posterior direction, the first anatomical reference member being connected to the reference mark positioning guide;
   a second anatomical reference member configured for placement against the anterior cortical bone of the femur and connected to the reference mark positioning guide opposite the first anatomical reference member;
   an adjustment mechanism engaged with the reference mark positioning guide and configured to be actuated to continuously displace, at least between standard femoral component sizes, the reference mark positioning guide in the anterior-posterior direction relative to the first and second anatomical referencing members so as to translationally adjust the position of the reference mark on the femur in the anterior-posterior direction, wherein the adjustment mechanism is configured to operatively engage and secure the reference mark positioning guide at least between standard femoral component sizes to facilitate placement of the reference mark in the femur; and
   a rod receiving member attached to the reference mark positioning guide and the anatomical referencing members, the rod receiving member defining a rod opening configured to slidingly receive an intramedullary rod therethrough, the intramedullary rod being received into a medullary canal of the femur and extending outwardly of the planed distal surface thereof and through the rod opening defined by the rod receiving member, the rod opening and the intramedullary rod received therethrough being complementarily configured to prohibit rotation of the rod receiving member about the intramedullary rod while the reference mark positioning guide is juxtaposed with the planed distal surface.

2. A femoral caliper of claim 1, wherein the rod receiving member is configured to translate with respect to the reference mark positioning guide and the anatomical referencing members.

3. A femoral caliper of claim 2, wherein the rod receiving member includes a locking mechanism that is configured to inhibit sliding movement of the rod receiving member relative to the intramedullary rod.

4. A femoral caliper of claim 1, wherein the reference mark positioning guide comprises a planar surface and an opening defined through the planar surface, the planar surface configured to lie flush to a corresponding planar distal surface of the femur.

5. A femoral caliper of claim 4, wherein the rod receiving member is positioned within the opening defined in the planar surface and is configured to guide the intramedullary rod substantially perpendicular to the planar surface.

\* \* \* \* \*